United States Patent [19]

Sierocuk et al.

[11] Patent Number: 4,891,851
[45] Date of Patent: Jan. 9, 1990

[54] FLEXIBLE PATIENT TRANSFER CRADLE

[75] Inventors: Thomas J. Sierocuk, New Berlin; Robert J. Dobberstein, West Allis, both of Wis.

[73] Assignee: General Electric Company, Milwaukee, Wis.

[21] Appl. No.: 560,301

[22] Filed: Dec. 12, 1983

[51] Int. Cl.⁴ .............................................. A61G 7/08
[52] U.S. Cl. ....................................... 5/81 R; 16/46; 5/82 R
[58] Field of Search .................... 5/81 R, 81 B, 81 C, 5/82 R, 82 B, 89, 83, 84, 85, 86, 87, 88; 16/18 R, 45, 46

[56] References Cited

U.S. PATENT DOCUMENTS

| | | | |
|---|---|---|---|
| 2,607,103 | 8/1952 | Davidson | 5/82 R |
| 3,094,117 | 6/1963 | Hintz | 5/82 R |
| 3,133,295 | 5/1964 | Klingensmith | 5/81 R |
| 3,372,405 | 3/1968 | Doering | 5/86 |
| 3,566,422 | 3/1971 | Klippel | 5/82 R |
| 3,611,454 | 10/1971 | Klippel | 5/82 R |
| 3,675,255 | 7/1972 | Johnsson | 5/82 R |
| 3,905,054 | 9/1975 | Windsor et al. | 5/81 R |
| 4,347,635 | 9/1982 | Eisenhauer | 5/82 R |

FOREIGN PATENT DOCUMENTS 2281237  4/1976  France ..................................... 16/46

Primary Examiner—Vinh Luong
Attorney, Agent, or Firm—Douglas E. Stoner

[57] ABSTRACT

A patient transfer cradle is made up of a flexible mounting plate which allows cradle wheels mounted to the underside of the plate to maintain contact with the rolling surface, whether it is level or not. A plurality of support rib members are disposed along the length of the mounting plate transversely relative to the long dimension of the plate. The ribs, which are secured to the upper surface of the mounting plate, are slidably engaged by a pair of elongated members which are coextensive with and disposed on either side of the plate. In this manner, the support ribs are capable of longitudinal movement relative to the elongated members permitting the cradle to flex without resistance from the elongated members.

6 Claims, 2 Drawing Sheets

FLEXIBLE PATIENT TRANSFER CRADLE

BACKGROUND OF THE INVENTION

This invention relates to medical diagnostic apparatus. More specifically, the invention relates to a flexible patient transfer cradle. The preferred embodiment of the cradle is disclosed herein, by way of example, with reference to nuclear magnetic resonance (NMR) apparatus.

A whole-body NMR system typically comprises a magnet, and a mobile patient support table capable of being secured to the magnet by means of a docking mechanism. In the preferred embodiment, the magnet is of superconductive construction configured as a solenoid having a longitudinal bore aproximately 90 cm. in diameter. Useful bore diameter for accommodating a patient is reduced to approximately 55 cm. by gradient, shim, and radio-frequency coil assemblies which are installed within the bore. A patient transfer cradle equipped with a plurality of wheels is provided to retrievably translate the patient, initially positioned atop the patient support table, into the magnet bore which has a bridge structure to support the weight of the cradle and the patient. A track fabricated on the bridge and top of support table engages bearings located on either side of a longitudinal groove formed on the underside of the patient cradle to guide the latter in its translational movement into and out of the bore. In a typical NMR system utilizing a 1.5 Tesla superconductive magnet, the total cradle travel range is approximately 300 cm. The cradle is designed to support a 300 lb. patient.

A problem experienced with conventional rigid cradles is the tendency of such cradles to wobble on two wheels when rolling on an unlevel support table or bridge surface. In use, the repeated transfer of the patient weight from 16 wheels in a typical cradle to 2 tends to cause premature failure of plastic ball bearings.

Another problem associated with cradles of conventional rigid design is the tendency of such cradles to move very roughly over small gaps and inclines. One such gap, transverse to the direction of travel, is between the bridge structure and the support table. Because cradle structure is rigid, each set of wheels is more likely to transmit to the patient mechanical shock due to such discontinuities. As a result, patient comfort is reduced.

It is, therefore, a principal object of the invention to provide a flexible patient transfer cradle capable of smooth movement on surfaces having irregularities.

It is a further object of the invention to provide a flexible patient transfer cradle which uniformly distributes the patient load to the roller bearings.

It is another object of the invention to provide a flexible patient transfer cradle which enhances patient comfort.

SUMMARY OF THE INVENTION

An inventive flexible patient transfer cradle is made up of an elongated, flexible mounting plate having a plurality of wheels mounted on the underside thereof. The mounting plate is sufficiently flexible to allow the wheels to maintain contact with an irregular surface to reduce the transmission of undesired vibrations to the patient. A plurality of support rib members are disposed along the length of the mounting plate transversely relative to the long dimension thereof. The ribs, which are secured to the upper surface of the mounting plate, are slidably engaged by a pair of elongated members which are coextensive with and disposed laterally on either side of the mounting plate. In this manner, the support ribs are capable of longitudinal movements relative to the elongated members, permitting the cradle to flex without resistance from the elongated members.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
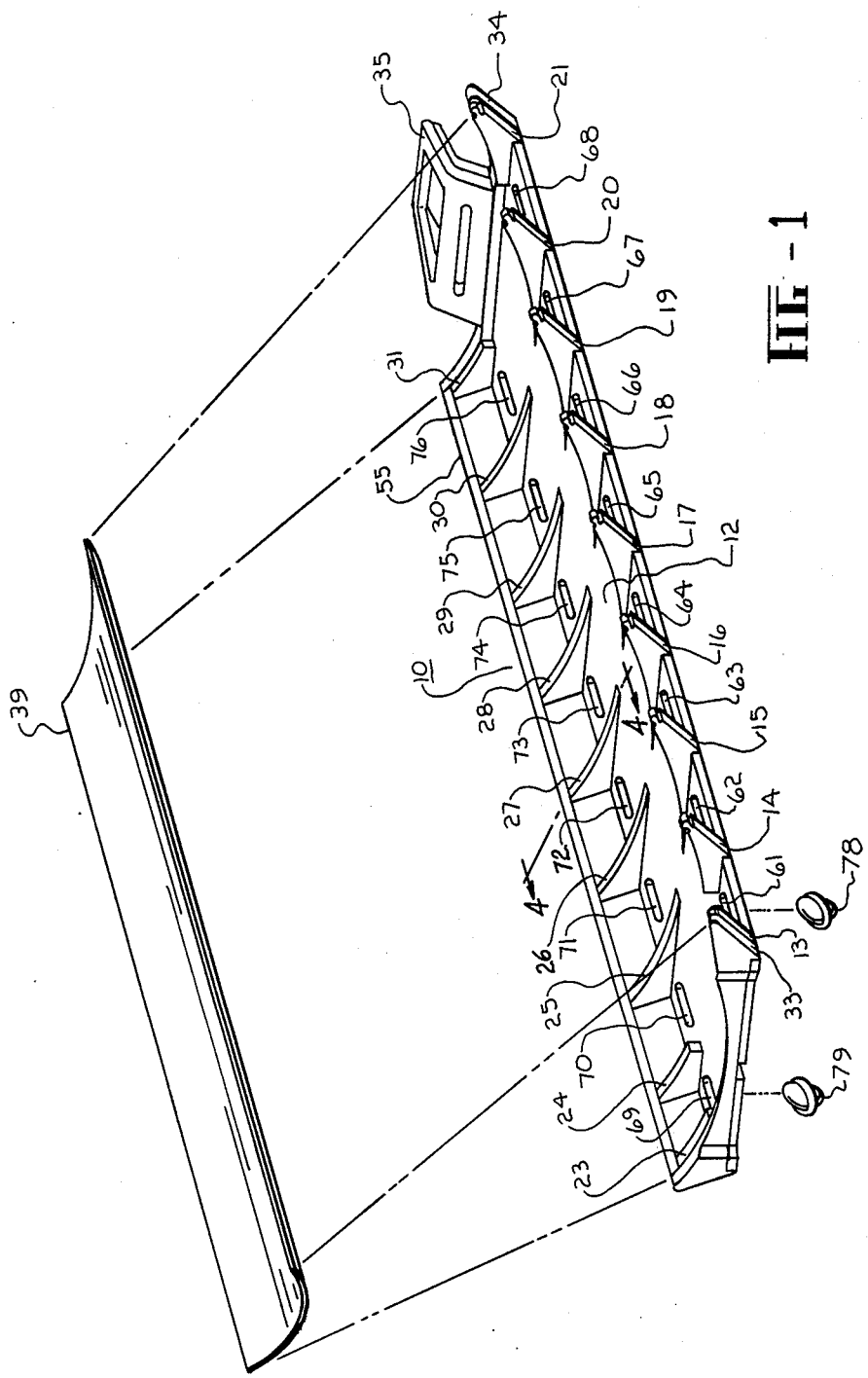
FIG. 1 is a perspective view of a partially disassembled inventive patient support cradle.

FIG. 1 depicts a partially disassembled patient transfer cradle in accordance with the invention. The cradle, generally designated 10, is made up of a flexible mounting plate 12 which in the preferred embodiment is fabricated from Lexan resin. The plate is sized to be 84 inches long and 13 inches wide by ½ inch thick so as to accommodate an adult patient, while preserving cradle flexibility. A plurality of transverse support ribs 13–21 and 23–31 are disposed along each longitudinal edge of the cradle. A pair of transverse end-support ribs 32 and 33 are secured to the mounting plate by means of adhesives, and/or by means of plastic or non-ferrous metallic screws. Transverse end support 34 is provided with an operator handle 35 to facilitate manipulation of the cradle.

It will be, of course, recognized that all of the support ribs 13–21 and 23–31 could be fabricated as single ribs, such as end ribs 33 and 34, although this would tend to reduce the flexibility of the mounting plate, unless the ribs are fashioned from suitably sized flexible materials.

Figure 2:
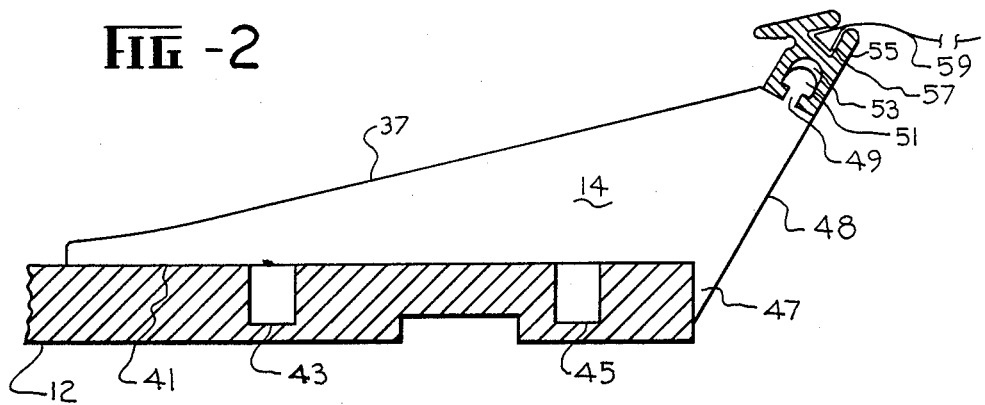
FIG. 2 depicts a single support rib, a plurality of which are utilized in the patient support cradle in accordance with the invention.

The detailed structure of a supporting rib will now be described by way of example with reference to rib 14 depicted in FIG. 2. The rib is generally configured in the shape of a wedge or triangle having a slightly concavely-curved upper edge 37 for supporting the convex lower surface of a support pad 39 shown in FIG. 1. Continuing with reference to FIG. 2, the lower edge or triangle base 41 of the support rib is provided with a pair of alignment pins 43 and 45 which engage a corresponding pair of alignment openings in mounting plate 12. A flange 47 extends from lower rib edge 41 and abuts against the edge of mounting plate 12 providing additional support.

The support rib is provided at the triangle apex where rib edges 37 and 48 meet with an extension 49 having an enlarged end-region 51 which slidably engages in "lock-and-key" fashion a complementarily-shaped opening 53 formed in one end of an elongated, interlocking member 55 shown in cross section. Member 55 is provided at its other end with an opening 57, similar to opening 53, which engages in lock-and-key fashion a patient restraining strap 59. As best seen in FIG. 1, interlocking member 55 is longitudinally coextensive with the cradle and is interlocked with each of support ribs 23-31. Although not shown, a similar interlocking member engages each of support ribs 13-21. In this manner, although the support ribs are fixedly secured to the flexible mounting plate, they are nonetheless able to move longitudinally relative to the interlocking members, such as the one designated 55, due to the lock-and-key interlock. This allows the cradle to flex when rolling over uneven surfaces without resistance from the interlocking members. In the preferred embodiment, member 55 is fabricated by an extrusion process.

Figure 3:
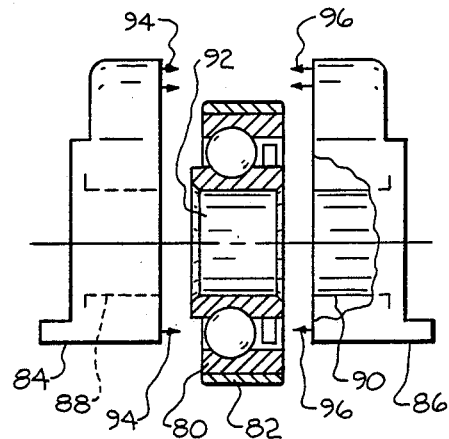
FIG. 3 illustrates an exemplary embodiment of a wheel housing suitable for use with the inventive patient transfer cradle.
Figure 4:
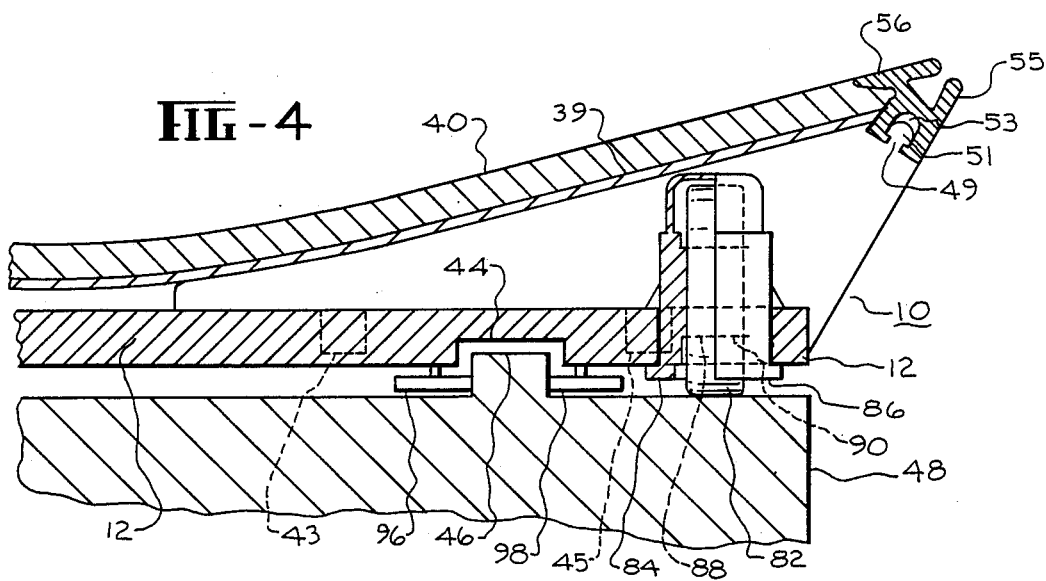
FIG. 4 is a cross-sectional view of the inventive patient support cradle.

Referring again to FIG. 1, mounting plate 12 is provided with a plurality of, for example, rectangular openings 61–68 between adjacent ones of support ribs 13–21. A similar set of openings 69–76 is formed between adjacent ones of support ribs 23–31. Each of the openings accommodates a wheel insert such as those designated 78 and 79 which are mounted in openings 61 and 69, respectively. As seen in FIG. 3, each of the wheel inserts comprises a low friction plastic ball bearing 80 (shown in cross section) having a soft, pliable tire 82 mounted thereon. The wheel is supported in a housing made up of two halves 84 and 86 having integral axel halves 88 and 90 which are sized to fit snugly into opening 92 in bearing 80. When the housing is assembled by bringing housing halves 84 and 86 together in the direction indicated by arrows 94 and 96, the wheel is substantially enclosed, as indicated in FIG. 4 which depicts an assembled wheel housing. For illustration, housing half 84 is shown partially cut away. In use, the flexible mounting plate allows all of the wheels to maintain contact with the rolling surface, whether it is level or not, minimizing the transmission of vibrations to the patient, and evenly distributing the patient weight. Uniform weight distribution to the wheels reduces instances of bearing overload and hence premature bearing failure.

Continuing with reference to FIG. 4, there is shown an integral cradle pad 40, comprised of a resilient foam material, mounted over a concave, rigid support member 39. The edges of the cradle pad and support member are held in place by an extension 56 formed in interlocking member 55 and which extends toward the center of the cradle. To preserve the flexibility of mounting plate 12, support member 39 is held in place solely by extension 56 and is not secured or bonded to the support ribs or other cradle parts.

As best seen in FIG. 4, cradle 10 is guided in its longitudinal travel by means of a plurality of bearings (such as those designated 96 and 98) mounted to mounting plate 12 on both sides of and along the length of channel 44. The bearings engage both sides of a track 46 projecting upward from patient support table 48, and a similar track (not shown) formed in the magnet bridge (not shown).

To minimize interaction with the magnetic fields produced in an NMR system, and to reduce interference with NMR data acquisition, all of the cradle parts are fabricated from non-ferrous, non-magnetic, non-hydroscopic, non-NMR active, radio-frequency-transparent materials. In the preferred embodiment, mounting plate 12 and support rib members 13–21 and 23–31 are fabricated from Lexan polycarbonate resin material. Interlocking member 55 comprises Noryl synthetic thermoplastic resin material, while end support rib members 33 and 34 are fabricated from polyethylene polymer material. Of course, it will be recognized that other suitable materials having the above-described properties may be advantageously utilized.

From the foregoing, it will be appreciated that in accordance with the invention there is provided a flexible patient cradle capable of smooth movement on irregular surfaces thereby to enhance patient comfort and reduce overloading of wheel bearings.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

We claim:

1. A flexible patient transfer cradle comprising:
    an elongate, flexible mounting plate having a plurality of wheels mounted to the underside thereof, said mounting plate being sufficiently flexible to allow said wheels to maintain contact with a rolling surface having irregularities therein to reduce the transmission of undesired vibrations to the patient;
    a plurality of support ribs disposed in two rows secured to the upper surface of said mounting plate, said support ribs in each row being positioned transversely and on either side of the longitudinal center line of said mounting plate along substantially the entire length thereof so as to substantially preserve the flexibility of said mounting plate; and
    a pair of parallel elongate members substantially coextensive with and disposed laterally on either side of said mounting plate, said elongated members slidably engaging said support ribs to enable longitudinal movement thereof relative to said elongate members, thereby allowing in use said cradle to bend without resistance from the elongate members.

2. The flexible patient transfer cradle of claim 1 wherein said wheels are each comprised of a plastic ball bearing having a soft, pliable tire mounted thereon, said wheels being supported within a wheel housing dimensioned to be accommodated within an opening formed in said mounting plate between adjacent ones of said support ribs, said flexible mounting plate allowing said wheels to maintain contact with a rolling surface having irregularities therein to uniformly distribute the patient weight thereby to avoid premature bearing failure.

3. The flexible patient transfer cradle of claim 1, wherein each of said support ribs is generally configured as a triangle, the base of which rests upon said mounting plate and wherein said support ribs each include a lock-and-key means at the triangle apex to slidably engage said elongate members.

4. The flexible patient cradle of claim 3 wherein said lock-and-key means comprises a projection at the apex of said triangle for engaging a complementarily-shaped opening in said elongated members.

5. The flexible patient transfer cradle of claim 4 wherein said pair of elongate members each includes a longitudinal projection extending toward the center line of the cradle to hold in place an integral cradle pad.

6. The flexible patient transfer cradle of claim 1 wherein each of said support ribs in said plurality comprises a single flexible support rib member having sufficient flexibility to permit said wheels mounted to said flexible mounting plate to maintain contact with an irregular rolling surface, said flexible support rib member being positioned transversely and across the longitudinal center line of said mounting plate.

* * * * *